US010105677B2

(12) United States Patent
Fish et al.

(10) Patent No.: US 10,105,677 B2
(45) Date of Patent: Oct. 23, 2018

(54) SORBENT

(71) Applicant: Johnson Matthey PLC, London (GB)

(72) Inventors: Andrew Fish, Stockton-on-Tees (GB); Lucy Jane Challis, Bishop Auckland (GB); Matthew John Cousins, Darlington (GB); Mark Robert Feaviour, Reading (GB); Alison Mary Wagland, Oxford (GB); Stephen David Pollington, Washington (GB); Edmund Hugh Stitt, Billingham (GB)

(73) Assignee: Johnson Matthey PLC, London, England (GB)

( * ) Notice: Subject to any disclaimer, the term of this patent is extended or adjusted under 35 U.S.C. 154(b) by 18 days.

(21) Appl. No.: 14/854,241

(22) Filed: Sep. 15, 2015

(65) Prior Publication Data
US 2016/0001258 A1 Jan. 7, 2016

Related U.S. Application Data

(63) Continuation of application No. 13/390,816, filed as application No. PCT/GB2010/051318 on Aug. 10, 2010, now Pat. No. 9,156,019.

(30) Foreign Application Priority Data

Aug. 17, 2009 (GB) .................... 0914272.0

(51) Int. Cl.
*B01J 20/02* (2006.01)
*B01D 53/64* (2006.01)
*B01J 20/06* (2006.01)
*B01J 20/08* (2006.01)
*B01J 20/28* (2006.01)
*B01J 20/30* (2006.01)
*B01J 20/34* (2006.01)
*B01D 15/20* (2006.01)
*B05D 1/02* (2006.01)
*B05D 1/18* (2006.01)
*C02F 1/28* (2006.01)
*C07C 7/12* (2006.01)
*C10G 25/00* (2006.01)
*C10L 3/10* (2006.01)
(Continued)

(52) U.S. Cl.
CPC .......... *B01J 20/0237* (2013.01); *B01D 15/20* (2013.01); *B01D 53/64* (2013.01); *B01J 20/0222* (2013.01); *B01J 20/0229* (2013.01); *B01J 20/0285* (2013.01); *B01J 20/06* (2013.01); *B01J 20/08* (2013.01); *B01J 20/2803* (2013.01); *B01J 20/28004* (2013.01); *B01J 20/28014* (2013.01); *B01J 20/28045* (2013.01); *B01J 20/28057* (2013.01); *B01J 20/28059* (2013.01); *B01J 20/28071* (2013.01); *B01J 20/28073* (2013.01); *B01J 20/28083* (2013.01); *B01J 20/28085* (2013.01); *B01J 20/3021* (2013.01); *B01J 20/3042* (2013.01); *B01J 20/3078* (2013.01); *B01J 20/3204* (2013.01); *B01J 20/3236* (2013.01); *B01J 20/3433* (2013.01); *B01J 20/3458* (2013.01); *B05D 1/02* (2013.01); *B05D 1/18* (2013.01); *C02F 1/281* (2013.01); *C07C 7/12* (2013.01); *C10G 25/00* (2013.01); *C10L 3/101* (2013.01); *B01D 2253/1128* (2013.01); *B01D 2253/342* (2013.01); *B01D 2255/20761* (2013.01); *B01D 2257/602* (2013.01); *B01J 20/32* (2013.01); *B01J 2220/56* (2013.01); *C02F 2101/20* (2013.01); *C10L 2290/542* (2013.01)

(58) Field of Classification Search
CPC .... B01J 20/32; B01J 20/0237; B01J 20/0222; B01J 20/0229; B01J 20/0285; B01J 20/06; B01J 20/08; B01J 20/28004; B01J 20/28014; B01J 20/2803; B01J 20/28085; B01J 20/3021; B01J 20/3042; B01J 20/203078; B01J 20/3204; B01J 20/3236; B01J 20/3433; B01J 20/3458; B01D 15/20; B01D 53/64; B05D 1/02; B05D 1/18; C02F 1/281; C07C 7/12; C01G 25/00; C10L 3/101
USPC .......................... 210/661, 688, 679; 502/214
See application file for complete search history.

(56) References Cited

U.S. PATENT DOCUMENTS 3,812,652 A 5/1974 Carr et al.
4,094,777 A 6/1978 Sugier et al.
(Continued)

FOREIGN PATENT DOCUMENTS

CN 1293594 5/2001
EP 0 260 826 A1 3/1988
(Continued)

OTHER PUBLICATIONS

International Search Report dated Oct. 21, 2010, from PCT International Application No. PCT/GB2010/051318.

*Primary Examiner* — James Fiorito
(74) *Attorney, Agent, or Firm* — Baker & Hostetler LLP

(57) ABSTRACT

A method for preparing a sorbent composition includes the steps of:
applying, from a solution or a slurry, a layer of a copper compound on the surface of a support material, and drying the coated support material,
wherein the thickness of the copper compound layer on the dried support is in the range 1-200 μm.
The precursor may be converted to a sorbent suitable for removing heavy metals from liquids or gases by applying one or more sulphur compounds to sulphide the copper compound and form CuS.

21 Claims, No Drawings

(51) Int. Cl.
*B01J 20/32* (2006.01)
*C02F 101/20* (2006.01)

(56) References Cited

U.S. PATENT DOCUMENTS

| | | | |
|---|---|---|---|
| 4,593,148 A * | 6/1986 | Johnson | C07C 7/148 |
| | | | 208/212 |
| 5,080,799 A | 1/1992 | Yan | |
| 5,200,390 A | 4/1993 | Howng | |
| 5,659,107 A * | 8/1997 | Cheung | C07C 7/12 |
| | | | 585/820 |
| 5,716,899 A | 2/1998 | Guile et al. | |
| 6,100,210 A | 8/2000 | Ollivier et al. | |
| 8,598,072 B2 * | 12/2013 | Sato | B01D 15/00 |
| | | | 502/413 |
| 8,598,073 B2 * | 12/2013 | Gadkaree | B01D 53/228 |
| | | | 210/679 |
| 2007/0251389 A1 | 11/2007 | Katsir et al. | |
| 2008/0184884 A1 | 8/2008 | Jadhav | |
| 2008/0302240 A1 | 12/2008 | Stinson | |
| 2009/0155148 A1 | 6/2009 | Kanazirev | |
| 2010/0004119 A1* | 1/2010 | Gadkaree | B01D 53/64 |
| | | | 502/84 |

FOREIGN PATENT DOCUMENTS

| | | |
|---|---|---|
| JP | 61-242638 | 10/1986 |
| JP | 8-150320 | 6/1996 |
| JP | 9-510141 | 10/1997 |
| WO | WO 99/51340 | 10/1999 |
| WO | WO-2009/101429 A1 | 8/2009 |
| WO | WO-2010/061212 A1 | 6/2010 |

* cited by examiner

SORBENT

CROSS-REFERENCE TO RELATED APPLICATIONS

This application is a continuation of U.S. application Ser. No. 13/390,816, filed Jun. 15, 2012, which is a U.S. National Phase application of PCT International Application No, PCT/GB2010/051318, filed Aug. 10, 2010, and claims priority of British Patent Application No. 0914272.0, filed Aug. 17, 2009, the disclosures of both of which are incorporated herein by reference in their entireties for all purposes.

FIELD OF THE INVENTION

This invention relates to sorbents and in particular to metal sulphide absorbents suitable for capturing heavy metals, such as mercury, arsenic and antimony, from fluid streams.

BACKGROUND OF THE INVENTION

Mercury is found in small quantities in fluid streams such as hydrocarbon or other gas and liquid streams. Arsenic may also be found in small quantities in hydrocarbon streams. Mercury, in addition to its toxicity, can cause failure of aluminium heat exchangers and other processing equipment. Therefore there is a need to efficiently remove these metals from fluid streams, preferably as early as possible in the process flowsheet.

U.S. Pat. No. 4,094,777 discloses the use of a pre-sulphided absorbent comprising copper sulphide for the absorption of mercury from a natural gas stream containing mercury. The sorbent Is prepared by mixing a copper compound such as powdered copper hydroxycarbonate (also known as basic copper carbonate) with a support or dispersion material, for example a cement, and forming extrudates or granules. Alternatively the sorbent is prepared by impregnation of a support, such as alumina spheres, with a solution of a soluble compound of copper such as copper nitrate. The copper compound in the granules, extrudates or support is sulphided using hydrogen sulphide or a solution of a sulphide in water or in an organic solvent.

Whereas combining particulate copper carbonate with a particulate support or cement provides an effective sorbent, a considerable proportion of the copper can remain unavailable within the resulting extrudate or granule. Copper is now an expensive metal and it is desirable to provide sorbents with lower levels of Cu that retain the high capacity for heavy metals observed with the granulated or extruded products. Impregnated materials, such as copper-nitrate impregnated materials can require high sulphiding temperatures, or the addition of silver compounds in order to be fully sulphided, both of which are undesirable.

SUMMARY OF THE INVENTION

We have found a method that overcomes the problems of the previous preparative routes.

Accordingly the invention provides a method for preparing a sorbent composition, comprising the steps of:
(i) applying, from a solution or a slurry, a layer of a copper compound on the surface of a support material, and
(ii) drying the coated support material,
wherein the thickness of the copper compound layer on the dried support is in the range 1-200 μm.

The method may further comprise the step of applying one or more sulphur compounds to effect sulphidation of the copper compound to form copper (II) sulphide, CuS.

The invention further provides a sorbent composition obtainable by this method, comprising a sulphided copper compound in the form of a layer on the surface of a support material.

The invention further provides a process for removing a heavy metal from a process fluid comprising contacting a heavy metal-containing-containing process fluid with the sulphided sorbent.

DETAILED DESCRIPTION OF THE INVENTION

By the term "sorbent" we include adsorbent and absorbent.

The term "heavy metal" used herein means mercury, arsenic, lead, cadmium and antimony, but the sorbent of the present invention is particularly useful for removing mercury and arsenic, especially mercury from fluid streams.

The copper compound should be sulphidable, i.e. reactive with sulphur compounds to form copper (II) sulphide. CuS. Suitable copper compounds are one or more of copper hydroxycarbonate, copper nitrate, copper sulphate, copper acetate, amine complexes thereof, i.e. copper amine carbonate, copper amine nitrate, copper amine sulphate and copper amine acetate, copper-(II)-sulphide and copper oxide. Preferred copper compounds are copper carbonate compounds, such as basic copper carbonate. Copper nitrate and sulphate are less preferred due to the evolution of $HNO_3$ or $H_2SO_4$ compounds during any subsequent sulphiding step.

Unlike the granulated or extruded products, the copper content of the sorbent of the present invention is relatively low and is preferably in the range 0.5-20% by weight (expressed as copper present in the unsulphided material), more preferably 0.75-10% by weight, most preferably 0.75-5.0% by weight. Although this level is less than half and in some cases less than a third of the copper in granulated materials, the effectiveness has surprisingly been found to match these products in terms of mercury captured.

In the present invention, the total sulphidable metal content of the sorbent, other than copper, is preferably ≤5% by weight. This is so that the corresponding water-soluble metal sulphates are formed in sufficiently low levels not to cause an increase in pressure drop and deactivation as a result of dissolution-re-deposition and agglomeration during use where the process fluids contain free water. Preferably the total metal sulphide content in the sulphided sorbent, other than copper, is ≤1% wt, more preferably ≤0.5% wt, especially ≤0.1% wt. The contaminant metal sulphide may be one or more of calcium sulphide, zinc sulphide, iron sulphide, nickel sulphide, chromium sulphide and manganese sulphide. They may be introduced by contamination of the copper compound or support material. The low contaminant metal sulphide level may be achieved by the selection of high purity copper compound and support, and by the exclusion of contaminant metal compounds from the composition.

The copper compound is present as a layer on the surface of the support. The thickness of the layer in the dried material is in the range 1 to 200 μm (micrometers), but preferably is in the range 1-150 micrometers, more preferably 1-100 micrometers, particularly 1-50 micrometers. Thinner layers make more efficient use of the applied copper. Sulphiding will typically leave the layer thickness unchanged or slightly thinner depending on the copper compound. The copper compound layer in the sorbent of the present invention may be readily fully sulphided.

The support material may be a ceramic or metal but preferably comprises an oxidic support such as an alumina, hydrated alumina, titania, zirconia, silica or aluminosilicate, or a mixture of two or more of these. Preferably the support has a relatively high surface area and porosity so that the surface area of the resulting layer may be maximised. Desirably the support has a BET surface area of 10-330 $m^2 \cdot g^{-1}$, preferably 100-330 $m^2 \cdot g^{-1}$, more preferably 130-330 $m^2 \cdot g^{-1}$. The pore volume is preferably 0.3-0.9 $cm^3 \cdot g^{-1}$, more preferably 0.4-0.9 $cm^3 \cdot g^{-1}$. The support may be macroporous, mesoporous or microporous but is preferably macroporous, i.e. it has an average pore diameter >50 nm, or mesoporous, i.e. is has an average pore diameter in the range 2-50 nm. In such materials preferably >50% of the pore volume arises from such pores. Macroporous materials are useful in the present invention because of their ability to hold copper compounds on their surface. The BET surface area may be conveniently measured using nitrogen physisorption. Pore volumes may also be determined using nitrogen physlsorpion, but in the present Invention as the pore volumes are relatively large, mercury porosimetry may be more suitably used. Pore diameters may also be determined using these techniques.

Preferred supports are aluminas such as gamma, theta and delta aluminas. In a particularly preferred embodiment, the support is a gamma alumina.

In the present invention, the copper compound is applied to the surface of the support. If the support Is porous, some of the copper compound may enter pores at or near the surface of the support. However the thickness of the layer of copper compound in the dried coated support should remain in the range 1-200 μm.

The support may be provided as a foam, monolith or honeycomb, or as a coating on a structured packing. Such supports offer a reduced pressure drop in sorbent vessels compared to spherical granulated sorbents. Particularly suitable foam supports are described in EP-A-0260826. Alternatively, the support may be in the form of shaped particulate unit selected from the group consisting of spheres, rings (e.g. Rashig rings), trilobes, quadralobes, and cylinders, which may be lobed or fluted, having between 2 and 10 holes extending therethrough. Shaped supports that provide the combination of reduced pressure drop combined with high strength are preferred. 4-hole cylinders, and rings are particularly preferred.

Particulate shaped units desirably have a minimum dimension, which may be the width, diameter or length, in the range 1-50 mm, and an aspect ratio (i.e. width or diameter/length) in the range 0.5-5 Units with a diameter or width in the range 3-10 mm are preferred for industrial scale sorbents, although 1-5 mm units may also be used.

The layer of copper compounds may be formed on the support in a number of ways. In one embodiment, a layer of copper carbonate is formed by applying a slurry, e.g. by dipping or spraying the support with a slurry, which may be aqueous or non aqueous, of an insoluble copper compound such as basic copper carbonate. The basic copper carbonate may be obtained commercially or prepared freshly by precipitating it from a copper salt solution using an alkaline carbonate precipitant, followed by washing to remove the corresponding alkaline metal salt. The basic copper carbonate is dispersed in a liquid medium, which is desirably aqueous. The solids content may conveniently be in the range 10-30% wt. Binder materials such as alumina or hydrated alumina sols may be included in the layer and other conventional wash-coat preparation techniques may be applied, such as milling and mixing of the dispersion to achieve the desired particle size prior to coating the support. The support may be coated by dipping the support into the slurry dispersion or by spraying the slurry dispersion of the copper carbonate compounds onto the support. Multiple dipping and/or spraying may be applied. The slurry may be applied to supports at temperatures in the range 10-95° C. or higher, preferably 10-50° C. We have found that the pH of the slurry can have an effect on the sulphur capacity and hence mercury capacity of the sorbent. Preferably the pH of the basic copper carbonate slurry is in the range 5-9.

In an alternative embodiment, the layer of copper compound is formed by applying a solution of a copper amine compound onto the support and simultaneously or subsequently heating the support to a temperature in the range 50-200° C. Copper amine compounds may be formed by dissolving copper compounds such as basic copper carbonate, copper acetate or copper nitrate in aqueous ammonia solutions optionally in the presence of ammonium salts, using known methods. For example, basic copper carbonate may be dissolved in a solution of ammonium carbonate and concentrated ammonia such that the $Cu:NH_3$ molar ratio is preferably at least 1:4. Heating the solution causes the evolution of ammonia and the deposition of copper compounds on the surface of the support. Unlike impregnation techniques, the use of a heated support that destabilises the copper amine compound on contact results in the formation of a layer of the copper compound on the surface of the support rather than permitting the copper to diffuse all the way through it. In the present invention, the heated support is preferably sprayed with a solution comprising copper amine carbonate. Alternatively the support may be dipped in the copper amine compound solution and removed, with heating of the support before or after dipping, although this is less preferred. It is not preferred to form a slurry of the support in the solution of copper amine compound as, upon heating, this could result in considerable amounts of unsupported copper compounds precipitating out of solution. In a preferred method, the support is heated to a temperature in the range 50-200° C. and a solution of copper amine compound, preferably copper amine carbonate, sprayed onto the heated support. This immediately forms a thin eggshell layer of copper compound on the surface of the support with evolution of ammonia.

The coated support is dried prior to sulphiding to remove any solvents that may interfere with the sulphiding reaction, e.g. water. However the drying temperature is preferably kept ≤200° C., more preferably ≤150° C. to avoid bulk decomposition of the copper compounds. The coated supports may conveniently be dried at about 70-105° C. in air for 1-16 hours.

Whereas the un-dried or dried material may be calcined to convert the copper compounds to copper (II) oxide, e.g. by heating it to a temperature in the range 250-500° C. in air or inert gas, this is not necessary, as we have found that the deposited copper compounds may be directly sulphided without this additional step.

The sulphiding step, which converts the copper compounds to copper (II) sulphide, CuS, may be carried out using conventional processes. Hence the sulphiding step may be performed by reacting the copper compound in the layer with a sulphur compound selected from hydrogen sulphide, alkali metal sulphide, ammonium sulphide, elemental sulphur or a polysulphide. Hydrogen sulphide is preferred. Using a hydrogen sulphide-containing gas mixture is considerably easier and faster than using alternatives such as solutions of sulphur or sulphur compounds such as polysulphides. The gas mixture may, if desired, contain other sulphur compounds such as carbonyl sulphide or volatile mercaptans. The sulphiding compounds are preferably used in a mixture with other gases. Inert gases such as nitrogen, helium or argon are a convenient means to control the process. Carbon dioxide may also be used. The sulphiding gas mixture is preferably free of reducing gases such as hydrogen and carbon monoxide, but these may be present where the sulphiding step is performed at temperatures below 150° C., particularly below 100° C. Hydrogen sulphide is preferably provided to the copper carbonate layer in gas streams at concentrations of 0.1 to 5% by volume. Sulphiding temperatures in the range 1-100° C. may be used.

The sulphiding step may be performed on the dried sorbent precursor composition ex-situ in a sulphiding vessel through which a sulphiding agent is passed, or the sulphiding step may be performed in situ, in which case an absorbent precursor is installed and undergoes sulphidation in the vessel in which it is used to absorb heavy metals. In-situ sulphiding may be achieved using a sulphiding agent stream or where the stream containing heavy metal also contains sulphur compounds, the heavy metal-containing stream itself. Where such concomitant sulphiding and heavy metal absorption occurs, the amount of sulphur compound that is present depends on the type of sulphur compound and metal compound used. Usually, a concentration ratio, as defined by the ratio of sulphur compound (expressed as hydrogen sulphide) concentration (v/v) to heavy metal concentration (v/v), of at least one, and preferably of at least 10 is used so that the precursor is sufficiently sulphided. Should the initial concentration of the sulphur compound in the feed stream be below the level necessary to establish the desired ratio of sulphur compound to heavy metal concentration then it is preferred that the concentration of the sulphur compound is increased by any suitable method.

The sorbent according to the present invention is preferably pre-sulphided where the fluid to be treated contains free water. Pre-sulphiding also avoids problems caused by the change in volume and strength of the sorbent that can accompany the sulphiding step.

The sulphided sorbents desirably have a BET surface area in the range 10 to 330 $m^2 \cdot g^{-1}$, preferably 100 to 330 $m^2 \cdot g^{-1}$, more preferably 130 to 330 $m^2 \cdot g^{-1}$, and a pore volume of 0.3 to 0.8 $cm^3 \cdot g^{-1}$, more preferably 0.4 to 0.7 $cm^3 \cdot g^{-1}$.

The present invention may be used to treat both liquid and gaseous fluids containing heavy metals, particularly mercury and arsenic, especially mercury. In one embodiment, the fluid is a hydrocarbon stream. The hydrocarbon stream may be a refinery hydrocarbon stream such as naphtha (e.g. containing hydrocarbons having 5 or more carbon atoms and a final atmospheric pressure boiling point of up to 204° C.), middle distillate or atmospheric gas oil (e.g. having an atmospheric pressure boiling point range of 177° C. to 343° C.), vacuum gas oil (e.g. atmospheric pressure boiling point range 343° C. to 566° C.), or residuum (atmospheric pressure boiling point above 566° C.), or a hydrocarbon-containing stream produced from such a feedstock by e.g. catalytic reforming. Refinery hydrocarbon steams also include carrier streams such as "cycle oil" as used in FCC processes and hydrocarbons used in solvent extraction. The hydrocarbon stream may also be a crude oil stream, particularly when the crude oil is relatively light, or a synthetic crude stream as produced from tar oil or coal extraction for example. Gaseous hydrocarbons may be treated using the process of the Invention, e.g. natural gas or refined paraffins or olefins, for example. Off-shore crude oil and off-shore natural gas streams in particular may be treated with the absorbent of the present invention. Contaminated fuels such as petrol or diesel may also be treated. Alternatively, the hydrocarbon may be a condensate such as natural gas liquid (NGL) or liquefied petroleum gas (LPG), a liquefied natural gas (LNG) or gases such as a coal bed methane, landfill gas or biogas.

Non-hydrocarbon fluids which may be treated according to the invention include carbon dioxide, which may be used in carbonated drinks, enhanced oil recovery processes, in carbon capture and storage, solvents for decaffeination of coffee, flavour and fragrance extraction, solvent extraction of coal etc. Fluids, such as alcohols (including glycols) and ethers used in wash processes or drying processes (e.g. triethylene glycol, monoethylene glycol, Rectisol™, Purisol™ and Selexol™), may be treated by the inventive process. Mercury may also be removed from amine streams used in acid gas removal units. Natural oils and fats such as vegetable and fish oils may be treated by the process of the invention, optionally after further processing such as hydrogenation or transesterification e.g. to form biodiesel.

Other fluid streams that may be treated include the regeneration gases from dehydration units, such as molecular sieve off-gases, or gases from the regeneration of glycol driers.

Feed streams which are susceptible to being treated by the absorbents may also include those which inherently contain both heavy metal and a sulphur compound e.g. certain natural gas streams, or a mercury- and/or arsenic-containing stream to which a sulphur compound has been added to effect mercury and arsenic absorption.

The present invention is of particular utility where the fluid contains free water, preferably in low levels in the range 0.02 to 1% vol. Higher levels up to 5% vol may be tolerated for short periods. The absorbents of the present invention may be regenerated simply after prolonged exposure to water simply by purging with a dry gas, preferably a dry inert gas such as nitrogen.

Preferably the absorption of mercury is conducted at a temperature below 150° C., preferably at or below 120° C. in that at such temperatures the overall capacity for mercury absorption is increased. Temperatures as low as 4° C. may be used to good effect in the present invention. A preferred temperature range is 10 to 60° C.

The mercury may be in the form of elemental mercury, or organomercuric, or organomercurous compounds. The present invention is particularly effective in removing elemental mercury although other forms of mercury may be removed for short periods. Typically the concentration of mercury in a gaseous feed stream is from 0.01 to 1100 $\mu g/Nm^3$, and more usually between 10 to 600 $\mu g/Nm^3$.

In use, the sorbent material may be placed in a sorption vessel and the fluid stream containing heavy metal is passed through it. Desirably, the sorbent is placed in the vessel as one or more fixed beds according to known methods. More than one bed may be employed and the beds may be the same or different in composition. The gas hourly space velocity through the absorbent may be in the range normally employed.

EXAMPLES

The invention is further described by reference to the following Examples. Unless otherwise stated, the following analytical tools were used;

i) Sulphur. Analysis for sulphur content was performed using a LECO SC632, by combustion and subsequent infrared measurement of sulphur dioxide.
ii) BET surface area and Pore Structure Analysis. These were determined using conventional nitrogen physisorption. The samples were out-gassed at 140° C. for 1 hour with a nitrogen purge prior to BET surface area/isotherm measurements.
iii) Mercury porosimetry. The samples were dried at 115° C. for 16 hours prior to introducing mercury into the pores under increasing pressure to determine pore volume.
iv) Copper content. Cu was measured using ICP-OES and calculated using conventional standards.
v) Cu carbonate thickness. The layer thickness was measured using electron-probe micro-analysis (EPMA). The samples were mounted in resin, polished and vacuum carbon coated before images were taken at an accelerating voltage of 20 kV.

Example 1

Washcoat of Basic Cooper Carbonate

Washcoat preparation: Basic copper carbonate (81 g) and Sasol Disperal P3 [a high purity dispersible alumina binder] (9 g) were added to 210 g of demineralised water. The slurry was mixed on a high-speed mixer and milled to obtain the desired particle size. The pH was 5.9 after milling and the particle size (d90) was 4.4 microns.

Spray Coating: 100 g of gamma-, delta-theta-, or alpha-alumina spheres (1 mm diameter) were loaded into a foil-lined pan coater and sprayed with 12 g of washcoat. The support was maintained at 25-65° C. throughout.

The coated support was dried for 16 hours at 105° C. The copper contents of the dried materials were 2.53-3.66% wt.

Sulphiding: 60 ml of coated material were fully sulphlided with 1% $H_2S$ in $N_2$. The flow rate of the gas was 42 litres $hr^{-1}$ and the sulphiding was carried out at ambient temperature and pressure.

Copper layer thicknesses of 25-50 μm were observed for the sulphided materials.

Example 2

Copper Amine Carbonate $[Cu(NH_3)_4(CO_3)]$

Ammonium carbonate (46.18 g, 0.294 mol) was dissolved in ammonia solution (100 ml, 1.8 mol) under gentle heating. Copper hydroxycarbonate (20.22 g, 9.98 g Cu, 0.17 mol) was added to the ammonium carbonate/ammonia solution and stirred to dissolve. The resulting solution was determined to contain 93.1 $g \cdot L^{-1}$ copper.

Gamma-, deta-theta- or alpha-alumina spheres (1 mm diameter) were heated to either 50° C., 80° C. or 150° C. and sprayed with the Cu amine carbonate solution.

The coated support was dried for 16 hours at 105° C. The copper content of the dried materials was 0.98-1.46.% wt.

The coated materials were sulphided using the method of Example 1.

The copper layer thicknesses on the dried gamma-alumina supported material were measured by EPMA to be about 47 μm in each case. The dried delta-theta alumina support had a copper layer thickness of 41 μm and the dried alpha alumina support had a copper layer thickness of 28 μm.

The experiment was repeated on the gamma alumina support at 120° C. but with subsequent calcination at 350° C. for 2 hours to convert the copper carbonate layer to copper oxide prior to sulphidation using the method of Example 1. The copper content of the calcined material was 3.33% wt The copper layer thickness on the sulphided oxidic material was observed to be in the range 20-40 μm.

Example 3

Copper Amine Carbonate/Acetate

Ammonium acetate (22.64 g, 0.294 mols) was dissolved in ammonia solution (100 ml, 0.9 mol). Basic copper carbonate $[Cu_2(OH_2)2CO_3]$ (221 g/mol, Alfa Aesar) (20.22 g, 9.98 g Cu, 0.17 mols) was added in portions with stirring.

An alumina support, gamma alumina spheres (1 mm diameter), was heated to 150° C. and sprayed with the copper amine carbonate/acetate solution.

The coated support was dried for 16 hours at 105° C. and calcined at 350° C. for 2 hours. The copper content of the calcined material was 0.78% wt.

The calcined material was sulphided using the method of Example 1.

The copper layer thickness on the dried gamma alumina support was 10 μm.

Example 4

Mercury Static Testing 30 ml n-hexane saturated with elemental mercury was diluted with 30 ml clean hexane to give a Hg concentration of 300-700 ppb (w/v), transferred to a 100 ml conical flask with a PTFE magnetic stirrer bar and stirred on a medium-speed setting for 5 minutes. 0.50 g of each test material was weighed out and added into the conical flask. The suspension was stirred for 20 minutes on a medium setting to avoid the formation of fine particles. Samples of the suspension were taken over 20 minutes and analysed by atomic fluorescence on a PSA modified Hewlett Packard 6890 GC for elemental mercury quantification. The first order rate constant, k ($min^{-1}$), was determined as the gradient of a plot of $ln(Hg_o/Hg_x)$ against reaction time.

Samples prepared according to the methods of Examples 1-3 were tested using the above method. The results are set out below.

| Material Number | Cu (% wt) by ICPOES | Alumina Phase | Support | Copper Loading Technique | Copper Form pre-sulphiding | Rate Constant, k ($min^{-1}$) |
|---|---|---|---|---|---|---|
| 1 | 3.66 | γ | Spheres | Example 1 | Carbonate | 0.75 |
| 2 | 2.95 | θ-δ | Spheres | Example 1 | Carbonate | 0.33 |
| 3 | 2.53 | α | Spheres | Example 1 | Carbonate | 0.38 |
| 4 | 1.08 | γ | Spheres | Example 2 sprayed at 150° C. | Carbonate | 0.38 |
| 5 | 1.07 | γ | Spheres | Example 2 sprayed at 80° C. | Carbonate | 0.41 |
| 6 | 1.46 | γ | Spheres | Example 2 sprayed at 50° C. | Carbonate | 0.52 |

| Material Number | Cu (% wt) by ICPOES | Alumina Phase | Support | Copper Loading Technique | Copper Form pre-sulphiding | Rate Constant, k (min$^{-1}$) |
|---|---|---|---|---|---|---|
| 7 | 3.33 | γ | Spheres | Example 2 sprayed at 120° C. | Oxide | 0.39 |
| 8 | 0.78 | γ | Spheres | Example 3 | Oxide | 0.47 |
| 9 | 0.98 | θ-δ | Spheres | Example 2 sprayed at 150° C. | Carbonate | 0.41 |
| 10 | 1.15 | α | Spheres | Example 2 sprayed at 150° C. | Carbonate | 0.46 |

The best result was obtained with sprayed slurry of basic copper carbonate on gamma alumina. The mercury concentrations with time exposed to the materials are given below.

| Material Number | Hg Concentration (ppb w/v)/Sample Number | | | | | | | Removal (%) |
|---|---|---|---|---|---|---|---|---|
| | 0 | 1 | 2 | 3 | 4 | 5 | 6 | |
| 1 | 380 | 187 | 89 | 19 | 0 | 0 | 0 | 100 |
| 2 | 292 | 190 | 153 | 90 | 39 | 5 | 0 | 100 |
| 3 | 295 | 186 | 131 | 69 | 20 | 0 | 0 | 100 |
| 4 | 330 | 190 | 127 | 54 | 12 | 4 | 0 | 100 |
| 5 | 314 | 188 | 130 | 67 | 21 | 2 | 0 | 100 |
| 6 | 273 | 147 | 89 | 31 | 7 | 0 | 0 | 100 |
| 7 | 361 | 240 | 158 | 88 | 33 | 3 | 0 | 100 |
| 8 | 271 | 158 | 99 | 39 | 10 | 0 | 0 | 100 |
| 9 | 282 | 180 | 120 | 57 | 15 | 0 | 0 | 100 |
| 10 | 296 | 176 | 122 | 52 | 11 | 0 | 0 | 100 |

Material 1 was analysed to assess porosity in comparison with commercially available granulated copper-zinc oxide/alumina mercury sorbent. The results were as follows;

| Material Number | Cu (% wt) by ICPOES | Alumina Phase | Nitrogen Physisorption BET Surface Area (m$^2$g$^{-1}$) | |
|---|---|---|---|---|
| | | | Fresh | Sulphided |
| 1 | 3.66 | γ | 149.7 | 148.9 |
| Comparative | 43.2** | — | 59.5 | 53.6 |

**Derived from mass balance calculation

The difference in BET surface area for the product prepared according to the invention can be clearly seen. For measuring pore structure, Mercury porosimetry is more applicable for mesopores and in conjunction with N$_2$ physisorption gives a clearer indication of pore structure.

| | Mercury Porosimetry | | | | | |
|---|---|---|---|---|---|---|
| | Corrected Intrusion Volume (cm$^3$g$^{-1}$) | | Hg Entrapment (%) | | Mean Pore Diameter (nm) | |
| Material | Fresh | Sulph | Fresh | Sulph | Fresh | Sulph |
| 1 | 0.40 | 0.41 | 26 | 27 | 9 | 9 |
| Comparative | 0.34 | 0.34 | 49 | 90 | 40 | 38 |

The material 1 is mesoporous by this measurement.

Example 5

Flowing Tests

Materials 1, 6 and a commercially available granulated copper-zinc oxide/alumina product for comparison, were sulphided to saturation in 1% H$_2$S/N$_2$. 25 ml of the sulphided sorbent was charged to a tubular lab-scale absorption vessel (i.d. 19 mm). N-hexane saturated with elemental mercury to ca. 1.2 ppm (w/v) was passed through the bed at ambient temperature (about 25° C.), at a Liquid Hourly Space Velocity (LHSV) of 7.0 hr$^{-1}$. Samples were taken from the reactor exit line and analysed by atomic fluorescence on a PSA modified Hewlett Packard 6890 GC to monitor mercury levels. At the end of the test, the bed was discharged into 9 equivalent discrete sub-beds by vacuum, which were analysed for total mercury content (w/w) by ICP-Optical Emission Spectroscopy.

All materials were run for 750 hours with no consistent mercury slip observed in the exit stream. The results of the analysis of the recovered materials are given below.

| Bed # | Cumulative Bed Volume (ml) | | | Total Mercury (ppm w/w) | | |
|---|---|---|---|---|---|---|
| | 1 | 6 | Comp. | 1 | 6 | Comp. |
| 1 | 2.26 | 2.38 | 2.59 | 52260 | 24660 | 44380 |
| 2 | 5.31 | 4.72 | 4.47 | 22500 | 22900 | 8720 |
| 3 | 7.52 | 7.95 | 7.06 | 385 | 15170 | 715 |
| 4 | 10.51 | 10.85 | 9.53 | 0 | 1790 | 30 |
| 5 | 13.49 | 14.05 | 12.32 | 0 | 55 | 0 |
| 6 | 16.55 | 17.25 | 14.42 | 0 | 0 | 0 |
| 7 | 19.80 | 20.20 | 17.20 | 0 | 15 | 0 |
| 8 | 23.43 | 22.97 | 20.31 | 0 | 15 | 0 |
| 9 | 25.65 | 25.35 | 25.00 | 10 | 25 | 0 |

Material 1 shows superior mercury pickup to the commercially available product, on the inlet bed, at 4.5-5 wt % Hg. The profile is also sharp, with the majority of mercury removed by the inlet two beds and the remainder used to remove the mercury down to trace levels. Material 6 appears to be reaching saturation at ca. 2.5 wt % Hg, resulting in the different profile shape.

Example 6

Effect of pH

Two sorbents were prepared according to the method of Example 1 by spray coating a slurry washcoat of basic copper carbonate onto 1 mm gamma alumina spheres. The copper contents of both were virtually identical at 3.6% wt. The only difference was in the pH of the basic copper carbonate slurry washcoat. With material 1, the pH was 6.0-6.5. With material 11, the pH was raised with tetramethylammonium hydroxide to 10.0 In order to thin the slurry for spray-coating.

Assuming 100% conversion of the carbonate on sulphiding, this should result in 1.8% wt sulphur loading for both materials. However, the actual sulphur loadings achieved were Material 1=1.57% S (87% conversion)

Material 11=0.69% S (38% conversion)

The bed profiles during flowing testing were also very different, with material 11 appearing to have reached saturation on the inlet beds as indicated below.

| Bed | Cumulative Bed Volume (ml) | | Total Mercury (ppm w/w) | |
|---|---|---|---|---|
|  | 1 | 11 | 1 | 11 |
| 1 | 2.26 | 3.03 | 52260 | 13510 |
| 2 | 5.31 | 6.08 | 22500 | 13200 |
| 3 | 7.52 | 8.84 | 385 | 11730 |
| 4 | 10.51 | 11.28 | 0 | 9610 |
| 5 | 13.49 | 13.41 | 0 | 7945 |
| 6 | 16.55 | 16.42 | 0 | 4725 |
| 7 | 19.80 | 19.77 | 0 | 1335 |
| 8 | 23.43 | 22.74 | 0 | 175 |
| 9 | 25.65 | 25.47 | 0 | 25 |

The pH 6-6.5 material proved superior to the material applied at pH 10.

Example 7

Macroporous Material

Washcoat preparation: A basic copper carbonate washcoat slurry was prepared according to the method of Example 1.

Coating: A macroporous alpha alumina support material in the form of rings with an outer diameter of 15 mm, surface area 0.4 $m^2$/g and pore volume 0.09 $cm^3$/g was used. 30 g of the alumina support was dipped into the washcoat slurry for 10 minutes to coat the surface. The coated support was dried for 16 hours at 105° C. The coated rings were crushed to a particle size of 1-2 mm. The copper content of the dried material was 3.5% wt Sulphiding: 20 ml of the crushed material were fully sulphided with 1% $H_2S$ in $N_2$. The flow rate of the gas was 42 litres $hr^{-1}$ and the sulphiding was carried out at ambient temperature and pressure.

The resulting material was tested for mercury removal from n-hexane in a flowing test according to the method of Example 5. The material was run for 750 hours with no consistent mercury slip observed in the exit stream. The results of the analysis of the recovered material are given below.

| Bed | Cumulative Bed Volume (ml) | Total Mercury (ppm w/w) |
|---|---|---|
| 1 | 2.95 | 17530 |
| 2 | 5.93 | 10560 |
| 3 | 8.56 | 2535 |
| 4 | 11.93 | 660 |
| 5 | 14.51 | 260 |
| 6 | 17.02 | 210 |
| 7 | 20.07 | 200 |

The profile is sharp, with the majority of mercury removed by the Inlet two beds and the 1 remainder used to remove the mercury down to trace levels.

Example 8

Gas Phase Testing

A sulphided sorbent material was prepared according to the method of Example 1. The copper content of the sulphided sorbent was approximately 2% wt.

The ability of the sorbent to capture mercury in the gas phase was determined as follows: 4 ml of sorbent material was charged to a glass reactor of Internal diameter 5 mm. Nitrogen gas containing ~17 ppb (w/v) of elemental mercury vapour was passed downwards over the sorbent material at atmosperic pressure and ambient temperature at a GHSV of 400 $hr^{-1}$. The test was left under these conditions for 1173 hours. At the end of the test, the reactor was purged with clean nitrogen gas before discharging the sorbent material from the reactor. The sorbent was analysed for mercury content by acid digestion followed by ICP-OES analysis. The results show >2% by weight mercury capture with a sharp profile through the bed.

What is claimed:

1. A sorbent composition comprising an eggshell layer consisting of at least one copper compound and a binder material of alumina or hydrated alumina on the exterior surface of a support material, wherein:
   the support material is in the form of a shaped particulate unit with a diameter or width in the range of 1-10 mm,
   the eggshell layer has a thickness in the range of 1-200 μm, and
   the sorbent composition comprises 0.5 to 20% by weight of copper.

2. The sorbent composition according to claim 1, wherein the at least one copper compound comprises copper (II) sulphide.

3. The sorbent composition according to claim 1, wherein the at least one copper compound is basic copper carbonate or copper (II) oxide.

4. The sorbent composition according to claim 1, wherein the support material comprises an alumina, hydrated alumina, titania, zirconia, silica or aluminosilicate, or a mixture of two or more of these.

5. The sorbent composition according to claim 1, wherein the support material is an alumina.

6. The sorbent composition according to claim 1 wherein the support material is in the form of shaped particulate unit that is a sphere, ring, trilobe, quadralobe, or cylinder.

7. The sorbent composition according to claim 6, wherein the support material has between 2 and 10 holes extending therethrough.

8. The sorbent composition according to claim 1, wherein the support material has a BET surface area in the range of 10-330 $m^2 \cdot g^{-1}$ and a pore volume in the range of 0.3-0.9 $cm^3 \cdot g^{-1}$.

9. The sorbent composition according to claim 1, wherein the thickness of the layer is in the range of 1 to 150 μm.

10. The sorbent composition according to claim 1, wherein the sorbent comprises 0.75-10% by weight of copper.

11. A process for removing a heavy metal from a process fluid comprising contacting said fluid with a sorbent of claim 2.

12. A process for removing a heavy metal from a fluid comprising contacting said fluid with a sorbent composition of claim 3 wherein the fluid further comprises one or more sulphur compounds.

13. The process according to claim 11 wherein the heavy metal is mercury and/or arsenic.

14. The process according to claim 11 wherein the fluid is a hydrocarbon stream.

15. The process according to claim 12 wherein the heavy metal is mercury and/or arsenic.

16. The process according to claim 12 wherein the fluid is a hydrocarbon stream.

17. A sorbent composition comprising a layer on the exterior surface of a support material, the layer consisting of at least one copper compound and a binder material of alumina or hydrated alumina and having a thickness in the range 1-200 μm, wherein the support material is in the form of a shaped particulate unit with a diameter or width in the range 1-10 mm, the sorbent composition comprises 0.5 to 20% by weight of copper, and wherein the sorbent composition is obtained by
  (i) forming a slurry of basic copper carbonate and a dispersible alumina binder material and milling the slurry,
  (ii) applying the slurry on an exterior surface of the support material by dipping or spraying to form a coated support material, and
  (iii) drying the coated support material to form the sorbent composition.

18. The sorbent composition of claim 1, wherein the support material is in the form of a shaped particulate unit with a diameter or width in the range of 3-10 mm.

19. The sorbent composition of claim 17, wherein the support material is in the form of a shaped particulate unit with a diameter or width in the range of 3-10 mm.

20. The sorbent composition of claim 17, wherein the layer has a thickness in a range of 1-150 μm.

21. The sorbent composition of claim 1, wherein the binder material is alumina.

\* \* \* \* \*